US012564446B2

(12) United States Patent
Rock et al.

(10) Patent No.: US 12,564,446 B2
(45) Date of Patent: Mar. 3, 2026

(54) SYSTEMS AND METHODS FOR PLANNING AND ASSISTING ORTHOPAEDIC SURGICAL PROCEDURES

(71) Applicant: DEPUY IRELAND UNLIMITED COMPANY, Ringaskiddy (IE)

(72) Inventors: Michael J. Rock, Leeds (GB); Alasdair Mercer, Leeds (GB); David R. Wolfson, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 454 days.

(21) Appl. No.: 18/092,257

(22) Filed: Dec. 31, 2022

(65) Prior Publication Data

US 2024/0216066 A1     Jul. 4, 2024

(51) Int. Cl.
*A61B 34/10*          (2016.01)
*A61B 17/15*          (2006.01)

(52) U.S. Cl.
CPC ............ *A61B 34/10* (2016.02); *A61B 17/154* (2013.01); *A61B 2034/104* (2016.02); *A61B 2034/105* (2016.02)

(58) Field of Classification Search
CPC ... A61B 17/154; A61B 17/155; A61B 17/157; A61B 17/56; A61B 2017/564; A61B 2017/567; A61B 2017/568; A61B 2034/108; A61B 34/10; A61B 34/30; A61B 34/25; A61B 2034/104; A61B 2034/105
See application file for complete search history.

(56) References Cited

U.S. PATENT DOCUMENTS

| | | | |
|---|---|---|---|
| 6,205,411 | B1 | 3/2001 | DiGioia, III et al. |
| 8,010,180 | B2 | 8/2011 | Quaid et al. |
| 8,771,365 | B2 | 7/2014 | Bojarski et al. |
| 8,926,706 | B2 | 1/2015 | Bojarski et al. |
| 9,020,788 | B2 | 4/2015 | Lang et al. |
| 9,101,394 | B2 | 8/2015 | Arata et al. |

(Continued)

FOREIGN PATENT DOCUMENTS

| | | |
|---|---|---|
| WO | 2017106294 A2 | 6/2017 |
| WO | 2021170591 A1 | 9/2021 |
| WO | 2024008923 A1 | 1/2024 |

OTHER PUBLICATIONS

Gary W. Doan, et al, Image-Free Robotic-Assisted Total Knee Arthroplasty Improves Implant Alignment Accuracy: A Cadaveric Study, The Journal of Arthroplasty 37 (2022) 795-801.

(Continued)

*Primary Examiner* — Samuel S Hanna
(74) *Attorney, Agent, or Firm* — Barnes & Thornburg LLP

(57) ABSTRACT

Systems and methods for planning and assisting orthopaedic surgical procedures include a computer system and a robotic surgical device. The computer system receives a set of target joint space values including a target extension space value and a target flexion space value. The computer system initializes a surgical plan including planned resection heights and determines a set of current joint space values based on the surgical plan. The computer system adjusts one or more planned resection heights of the surgical plan until the set of current joint space values matches the set of target joint space values. The computer system may control the robotic surgical device according to the surgical plan.

20 Claims, 10 Drawing Sheets

(56) References Cited

U.S. PATENT DOCUMENTS

| | | | |
|---|---|---|---|
| 9,364,291 | B2 | 6/2016 | Bellettre et al. |
| 9,387,079 | B2 | 7/2016 | Bojarski et al. |
| 9,603,711 | B2 | 3/2017 | Bojarski et al. |
| 9,665,686 | B2 | 5/2017 | Van Vorhis et al. |
| 9,826,981 | B2 | 11/2017 | Schoenefeld et al. |
| 9,827,051 | B2 | 11/2017 | Arata et al. |
| 9,913,692 | B2 | 3/2018 | Arata et al. |
| 9,916,421 | B2 | 3/2018 | Van Vorhis et al. |
| 10,064,685 | B2 | 9/2018 | Bellettre et al. |
| 10,813,574 | B2 | 10/2020 | Fleig et al. |
| 11,033,300 | B2 | 6/2021 | Pavlovskaia et al. |
| 11,147,627 | B2 | 10/2021 | Gangwar et al. |
| 11,158,415 | B2 | 10/2021 | Daley et al. |
| 11,376,072 | B2 | 7/2022 | Bellettre et al. |
| 11,744,643 | B2 | 9/2023 | Rossetto et al. |
| 11,759,216 | B2 | 9/2023 | Metcalfe et al. |
| 11,819,282 | B2 | 11/2023 | Pavlovskala, I et al. |
| 11,847,755 | B2 | 12/2023 | Park et al. |
| 11,890,058 | B2 | 2/2024 | Metcalfe et al. |
| 11,948,674 | B2 | 4/2024 | Daley et al. |
| 12,226,164 | B2 | 2/2025 | Ryals et al. |
| 2005/0251148 | A1 | 11/2005 | Friedrich et al. |
| 2007/0219561 | A1 | 9/2007 | Lavallee et al. |
| 2008/0269596 | A1 | 10/2008 | Revie et al. |
| 2010/0076563 | A1 | 3/2010 | Otto et al. |
| 2010/0153081 | A1 | 6/2010 | Bellettre et al. |
| 2012/0041446 | A1 | 2/2012 | Wong et al. |
| 2012/0165820 | A1 | 6/2012 | De Smedt et al. |
| 2016/0228193 | A1 | 8/2016 | Moctezuma de La Barrera et al. |
| 2017/0065350 | A1 | 3/2017 | Dossett et al. |
| 2017/0265944 | A1 | 9/2017 | Shupe et al. |
| 2018/0132949 | A1 | 5/2018 | Merette et al. |
| 2018/0233222 | A1 | 8/2018 | Daley et al. |
| 2018/0360544 | A1 | 12/2018 | Vanheule et al. |
| 2020/0345421 | A1 | 11/2020 | White et al. |
| 2022/0008207 | A1 | 1/2022 | Heldreth et al. |
| 2022/0031473 | A1* | 2/2022 | Carter .................... A61B 34/10 |
| 2022/0084652 | A1 | 3/2022 | Daley et al. |
| 2022/0183757 | A1 | 6/2022 | Caldera et al. |
| 2022/0183767 | A1 | 6/2022 | Otto et al. |
| 2022/0183774 | A1* | 6/2022 | Merette ................. G06T 11/206 |
| 2023/0080908 | A1 | 3/2023 | Ali et al. |
| 2023/0149090 | A1 | 5/2023 | Angibaud et al. |
| 2024/0008924 | A1 | 1/2024 | Dressler et al. |
| 2024/0008925 | A1 | 1/2024 | Dressler et al. |
| 2024/0216064 | A1 | 7/2024 | Ryals et al. |
| 2024/0245460 | A1 | 7/2024 | Utz et al. |
| 2024/0282427 | A1 | 8/2024 | Daley et al. |

OTHER PUBLICATIONS

Teruyuki Miyasaka, et al, Accuracy of Computed Tomography—Based Navigation-Assisted Total Knee Arthroplasty: Outlier Analysis, The Journal of Arthroplasty 32 (2017) 47-52.

Mustafa Citak, et al, Unicompartmental knee arthroplasty: Is robotic technology more accurate than conventional technique?, Elsevier The Knee 20 (2013) 268-271.

Saker Khamaisy, et al, Medial unicompartmental knee arthroplasty improves congruence and restores joint space width of the lateral compartment, Elsevier The Knee 23 (2016) 501-505.

H. Jacinto et al., "Multi-atlas automatic positioning of anatomical landmarks," Journal of Visual Communication and Image Representation, 2018, pp. 167-177, vol. 50, Elsevier.

European Patent Office, International Search Report and Written Opinion for related PCT/EP2023/087375, Apr. 23, 2024, 17 pages.

Brainlab AG, "Knee3 Surgical Technique," 2015, 58 pages.

Gibbons et al., "Development of a Statistical Shape-Function Model of the Implanted Knee for Real-Time Prediction of Joint Mechanics," Journal of Biomechanics, vol. 88, 2019, pp. 55-63.

Lambrechts et al., "Artificial Intelligence Based Patient-Specific Preoperative Planning Algorithm for Total Knee Arthroplasty," Frontiers in Robotics and AI, vol. 9, Mar. 8, 2022, 11 pages.

Depuy Synthes, VELYS Robotic-Assisted Solution for Total Knee, User Guide, Version 1.6, Rev. J, 2022, 217 pages.

Depuy Synthes, VELYS Robotic-Assisted Solution for Total Knee, User Guide, Version 1.5, Rev. F, 2021, 214 pages.

* cited by examiner

*700*

DETERMINE COMPONENT INITIAL POSITIONS
BASED ON SURGEON PREFERENCE    *702*

DETERMINE TIBIA, DISTAL FEMUR, AND
POSTERIOR FEMUR RESECTION HEIGHTS    *704*

DETERMINE CURRENT IMPLANT SPACES
IN EXTENSION (*E*) AND FLEXION (*F*)    *706*

COMPARE CURRENT *E*, *F*  TO TARGET *E*, *F*    *708*

*710*

AT TARGET?    YES

NO

FROM FIG. 7B         TO FIG. 7B         TO FIG. 7B

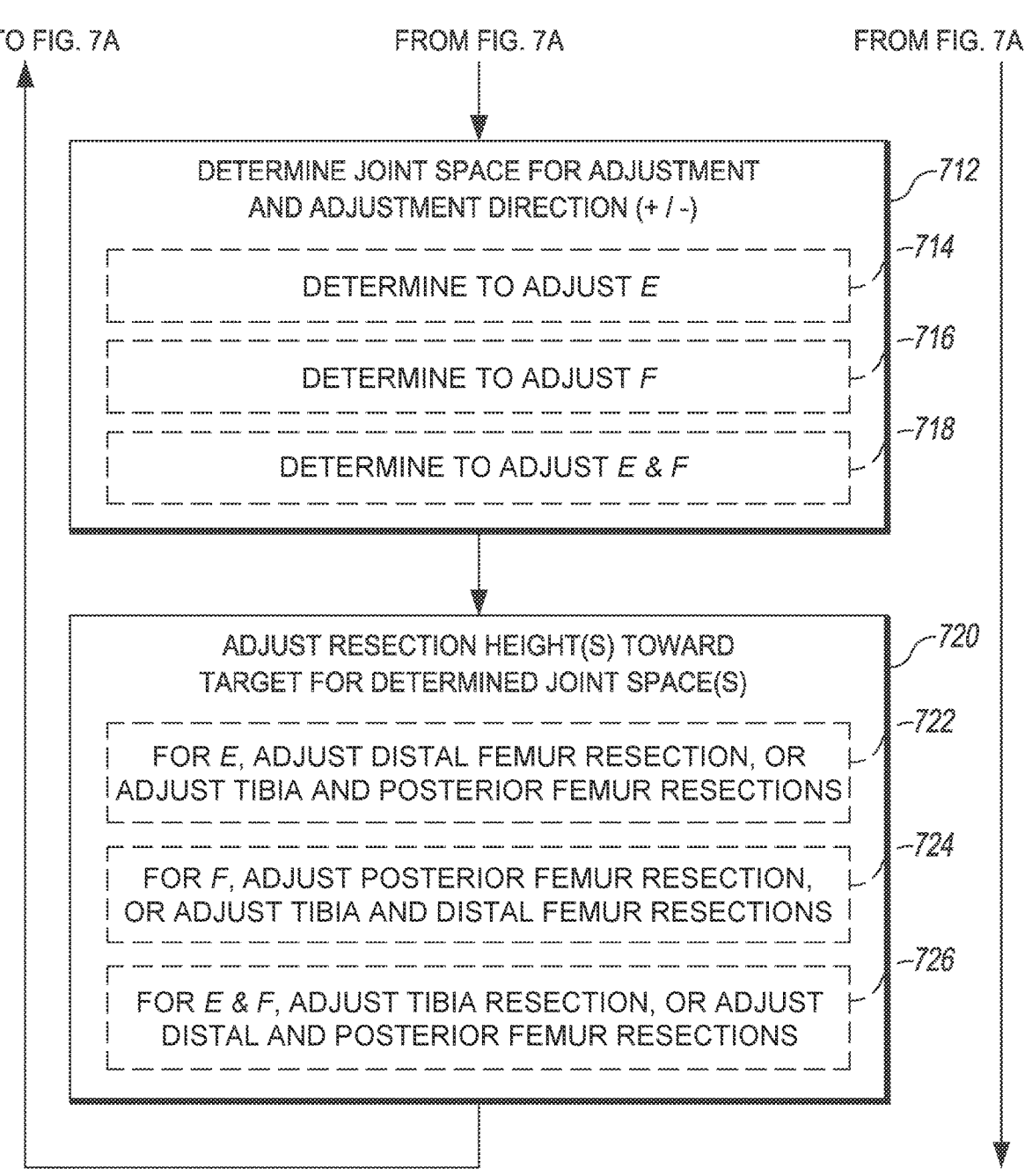

DETERMINE JOINT SPACE FOR ADJUSTMENT
AND ADJUSTMENT DIRECTION (+ / -)  — 712

DETERMINE TO ADJUST *E*  — 714

DETERMINE TO ADJUST *F*  — 716

DETERMINE TO ADJUST *E & F*  — 718

ADJUST RESECTION HEIGHT(S) TOWARD
TARGET FOR DETERMINED JOINT SPACE(S)  — 720

FOR *E*, ADJUST DISTAL FEMUR RESECTION, OR
ADJUST TIBIA AND POSTERIOR FEMUR RESECTIONS  — 722

FOR *F*, ADJUST POSTERIOR FEMUR RESECTION,
OR ADJUST TIBIA AND DISTAL FEMUR RESECTIONS  — 724

FOR *E & F*, ADJUST TIBIA RESECTION, OR ADJUST
DISTAL AND POSTERIOR FEMUR RESECTIONS  — 726

Fig. 7B

SYSTEMS AND METHODS FOR PLANNING AND ASSISTING ORTHOPAEDIC SURGICAL PROCEDURES

TECHNICAL FIELD

The present disclosure relates generally to orthopaedic surgical tools and systems and, more particularly, to systems and methods for automatically planning surgical parameters for use during an orthopaedic surgical procedure.

BACKGROUND

Joint arthroplasty is a well-known surgical procedure by which a diseased and/or damaged natural joint is replaced by a prosthetic joint, which may include one or more orthopaedic implants. For example, in a knee arthroplasty surgical procedure, a patient's natural knee joint is partially or totally replaced by a prosthetic knee joint. A typical prosthetic knee joint includes a tibial tray, a femoral component, and a polymer insert or bearing positioned between the tibial tray and the femoral component.

To facilitate the replacement of the natural joint with a prosthetic joint, orthopaedic surgeons may use a variety of orthopaedic surgical instruments such as, for example, surgical saws, cutting guides, reamers, broaches, drill guides, drills, positioners, insertion tools and/or other surgical instruments. For example, a surgeon may prepare a patient's tibia to receive the tibial tray by resecting the proximal femur with a surgical saw, and the surgeon may prepare the patient's femur to receive the femoral component by performing multiple resections of the distal femur with a surgical saw. A surgeon may use manual instruments such as cutting blocks or other cutting guides to perform the various resections in an orthopaedic procedure. Alternatively, or in addition, a surgeon may use a computer-assisted surgical navigation system, such as a robotic-assisted surgical system, to perform the various resections in an orthopaedic procedure.

SUMMARY

According to one aspect, a method for automatically generating a surgical plan for an orthopaedic surgical procedure may comprise receiving, by a computer system, a set of target joint space values, wherein the set of target joint space values comprises a target extension space value and a target flexion space value. The method may further comprise initializing, by the computer system, a surgical plan for the orthopaedic surgical procedure, wherein the surgical plan comprises planned resection heights including at least a distal femur resection height, a posterior femur resection height, and a tibia resection height. The method may also comprise determining, by the computer system, a set of current joint space values based on the surgical plan. The method may additionally comprise adjusting, by the computer system, one or more planned resection heights of the surgical plan until the set of current joint space values matches the set of target joint space values.

In some embodiments, the method may further comprise performing, by the computer system, bony registration of bony anatomy of a patient, and performing, by the computer system, leg-alignment registration on the patient. Determining the set of current joint space values may comprise determining the set of current joint space values based on the surgical plan, the bony registration, and the leg-alignment registration. Determining the set of current joint space values may comprise determining a current implant space in extension value as a function of the distal femur resection height and the tibia resection height. The current implant space in extension value may comprise the distal femur resection height, added to a bone space in extension value measured during the leg-alignment registration, added to the tibia resection height, less a distal femoral component thickness, and less a tibial component thickness. Determining the set of current joint space values may comprise determining a current implant space in flexion value as a function of the posterior femur resection height and the tibia resection height. The current implant space in flexion value may comprise the posterior femur resection height, added to a bone space in flexion value measured during the leg-alignment registration, added to the tibia resection height, less a posterior femoral component thickness, and less a tibial component thickness.

In some embodiments, adjusting the one or more planned resection heights of the surgical plan may comprise selecting a joint space for adjustment based on the current joint space value for the joint space not matching the target joint space value for the joint space, and selecting the one or more planned resection heights to adjust based on the joint space selected for adjustment. The joint space selected for adjustment may comprise an extension space, and adjusting the one or more planned resection heights may comprise one of (i) adjusting the distal femur resection height toward the target extension space value, or (ii) adjusting the tibia resection height toward the target extension space value and adjusting the posterior femur resection height to preserve a current flexion space value. The joint space selected for adjustment may comprise a flexion space, and adjusting the one or more planned resection heights may comprise one of: (i) adjusting the posterior femur resection height toward the target flexion space value, or (ii) adjusting the tibia resection height toward the target flexion space value and adjusting the distal femur resection height to preserve a current extension space value. The joint space selected for adjustment may comprise an extension space and a flexion space, and adjusting the one or more planned resection heights may comprise one of: (i) adjusting the distal femur resection height toward the target extension space value and adjusting the posterior femur resection height toward the target flexion space value, or (ii) adjusting the tibia resection height toward the target extension space value and the target flexion space value.

In some embodiments, adjusting the one or more planned resection heights may comprise selecting a first planned resection height having a lowest priority setting from among the distal femur resection height, the posterior femur resection height, and the tibia resection height, and adjusting the first planned resection height until a first boundary setting is met. In some embodiments, adjusting the one or more planned resection heights may further comprise, in response to the boundary setting being met, selecting a second planned resection height having a next-lowest priority setting from among the distal femur resection height, the posterior femur resection height, and the tibia resection height, and adjusting the second planned resection height until a second boundary setting is met. The boundary settings and the priority settings may reflect preferences of a surgeon performing the orthopaedic surgical procedure. The first boundary setting may comprise a minimum or a maximum resection height associated with the first planned resection height. The first boundary setting may comprise a minimum or a maximum varus/valgus angle or a minimum or a maximum hip-knee-ankle angle. The surgical plan may comprise planned medial resection heights and planned lateral resection heights, and the set of target joint space values may comprise medial target joint space values and lateral target joint space values.

In some embodiments, the method may further comprise controlling, by the computer system, a robotic surgical device to achieve the planned resection heights of the surgical plan. Controlling the robotic surgical device may comprise robotically constraining a surgical saw in a geometric plane defined by one of the planned resection heights of the surgical plan.

According to another aspect, an orthopaedic surgical planning system may comprise a computer system configured to initialize a surgical plan for the orthopaedic surgical procedure, wherein the surgical plan comprises planned resection heights including at least a distal femur resection height, a posterior femur resection height, and a tibia resection height. The computer system may be further configured to receive a set of target joint space values, wherein the set of target joint space values comprises a target extension space value and a target flexion space value. The computer system may be further configured to determine a set of current joint space values based on the surgical plan. The computer system may be further configured to adjust one or more planned resection heights of the surgical plan until the set of current joint space values matches the set of target joint space values.

In some embodiments, the computer system is further configured to perform bony registration of bony anatomy of a patient and to perform leg-alignment registration on the patient to measure a bone space in extension value and a bone space in flexion value. Determining the set of current joint space values may comprise determining a current implant space in extension value and a current implant space in flexion value. The current implant space in extension value may comprise the distal femur resection height, added to the bone space in extension value, added to the tibia resection height, less a distal femoral component thickness, and less a tibial component thickness. The current implant space in flexion value may comprise the posterior femur resection height, added to the bone space in flexion value, added to the tibia resection height, less a posterior femoral component thickness, and less a tibial component thickness.

In some embodiments, the computer system may be configured to adjust one or more planned resection heights of the surgical plan by selecting a first planned resection height having a lowest priority setting from among the distal femur resection height, the posterior femur resection height, and the tibia resection height, adjusting the first planned resection height until a first boundary setting is met, selecting, in response to the boundary setting being met, a second planned resection height having a next-lowest priority setting from among the distal femur resection height, the posterior femur resection height, and the tibia resection height, and adjusting the second planned resection height until a second boundary setting is met.

In some embodiments, the orthopaedic surgical planning system may further comprise a robotic surgical device configured to constrain movement of a surgical saw in a geometric plane defined by one of the planned resection heights of the surgical plan.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which:

FIGS. 7A and 7B are a simplified flow diagram of a method for automatically adjusting a surgical plan based on surgeon preferences that may be executed by the surgical planning and assistance device of FIG. 1;

DETAILED DESCRIPTION OF THE DRAWINGS

Figure 1:
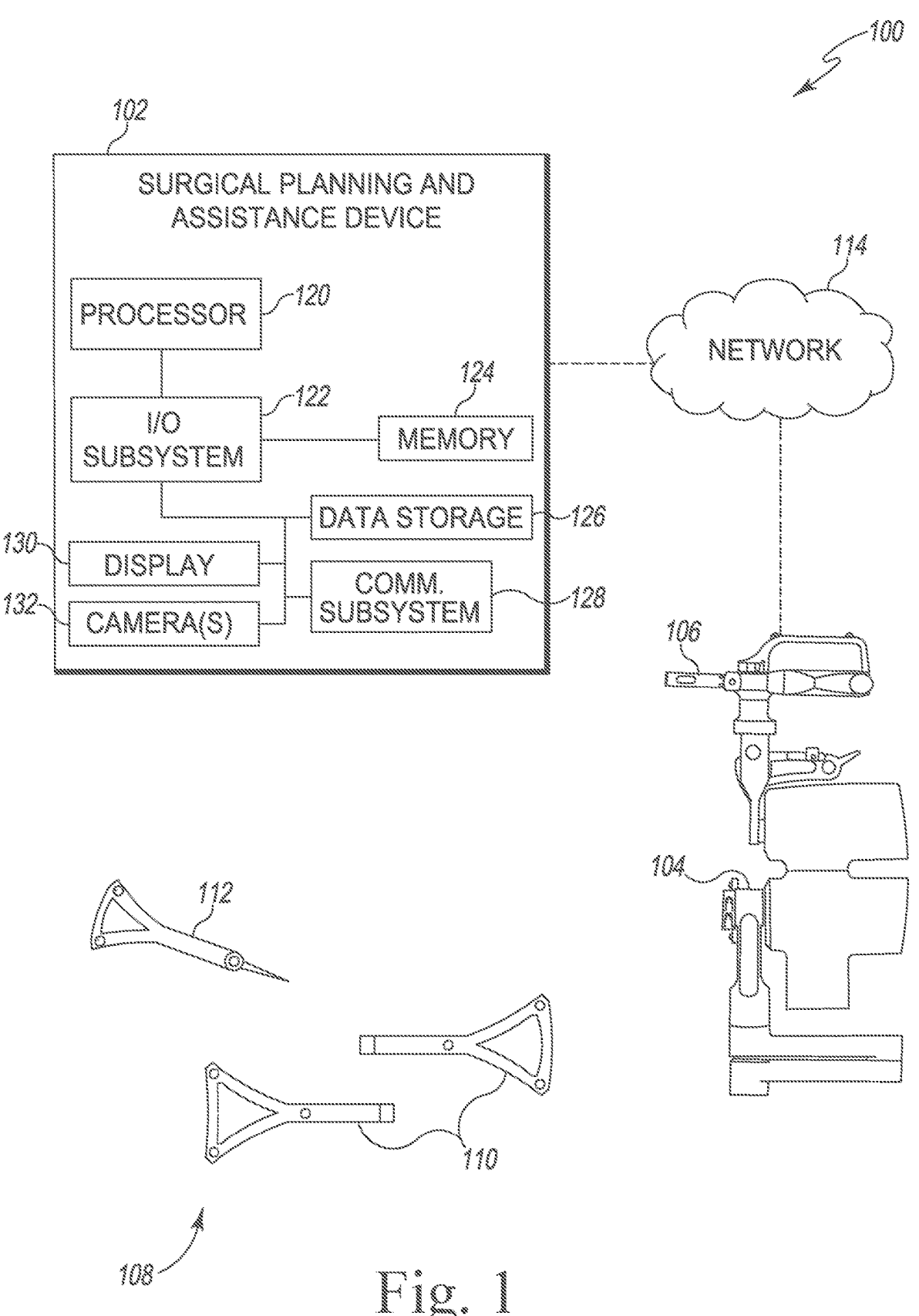
FIG. 1 is a schematic diagram of a system for planning and assisting an orthopaedic surgical procedure.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C).

Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, a surgical system 100 is used during an orthopaedic surgical procedure, which is illustratively a total knee arthroplasty (TKA) procedure. During that procedure, an orthopaedic surgeon performs registration of the patient's anatomy with the system 100. The surgeon or other user uses a surgical planning and assistance device 102 to automatically create a surgical plan based on joint space values provided by the surgeon. For example, the surgeon provides target extension space and flexion space values, which represent desired ligament balance for the knee joint after the surgical procedure, and the device 102 determines appropriate resection planes to achieve the target joint space values. A robotic surgical device 104 may be controlled based on the surgical plan during operation of the surgical procedure, for example by robotically constraining a surgical saw 106 to one or more resection planes defined by the surgical plan.

Thus, the system 100 provides improved automated surgical planning. The system 100 may determine a completed surgical plan more quickly and/or with less user intervention as compared to systems that require the surgeon to directly position or otherwise adjust the resection planes. Thus, the system 100 may provide for faster surgical planning and/or faster iteration times for surgical planning as compared to typical surgical planning systems.

As shown in FIG. 1, the system 100 includes the surgical planning and assistance device 102 and the robotic surgical device 104 as well as multiple registration targets 108. The surgical planning and assistance device 102 may be embodied as any type of computer system capable of performing the functions described herein. For example, the surgical planning and assistance device 102 may be embodied as, without limitation, a workstation, a desktop computer, a laptop computer, a special-purpose compute device, a server, a rack-mounted server, a blade server, a network appliance, a web appliance, a tablet computer, a smartphone, a consumer electronic device, a distributed computing system, a multiprocessor system, and/or any other computing device capable of performing the functions described herein. Additionally, although the surgical planning and assistance device 102 is illustrated in FIG. 1 as embodied as a single computer, it should be appreciated that the surgical planning and assistance device 102 may be embodied as multiple devices cooperating together to facilitate the functionality described below. For example, in some embodiments the system 100 may include a base station and a satellite station or other combination of computing devices. Additionally or alternatively, in some embodiments, the surgical planning and assistance device 102 may be embodied as a "virtual server" formed from multiple computer systems distributed across a network and operating in a public or private cloud.

As shown in FIG. 1, the illustrative surgical planning and assistance device 102 includes a processor 120, an I/O subsystem 122, memory 124, a data storage device 126, and a communication subsystem 128. Of course, the surgical planning and assistance device 102 may include other or additional components, such as those commonly found in a computer (e.g., various input/output devices), in other embodiments. Additionally, in some embodiments, one or more of the illustrative components may be incorporated in, or otherwise form a portion of, another component. For example, the memory 124, or portions thereof, may be incorporated in the processor 120 in some embodiments.

The processor 120 may be embodied as any type of processor or controller capable of performing the functions described herein. For example, the processor may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the surgical planning and assistance device 102 such as operating systems, applications, programs, libraries, and drivers. The memory 124 is communicatively coupled to the processor 120 via the I/O subsystem 122, which may be embodied as circuitry and/or components to facilitate input/output operations with the processor 120, the memory 124, and other components of the surgical planning and assistance device 102. For example, the I/O subsystem 122 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 122 may form a portion of a system-on-a-chip (SoC) and be incorporated, along with the processor 120, the memory 124, and other components of the surgical planning and assistance device 102, on a single integrated circuit chip.

The data storage device 126 may be embodied as any type of device or devices configured for short-term or long-term storage of data such as, for example, memory devices and circuits, memory cards, hard disk drives, solid-state drives, or other data storage devices. The communication subsystem 128 of the surgical planning and assistance device 102 may be embodied as any communication circuit, device, or collection thereof, capable of enabling communications between the surgical planning and assistance device 102 and remote devices. The communication subsystem 128 may be configured to use any one or more communication technology (e.g., wireless or wired communications) and associated protocols (e.g., Ethernet, Bluetooth®, Wi-Fi®, WiMAX, etc.) to effect such communication.

As shown in FIG. 1, the surgical planning and assistance device 102 includes a display 130. The display 130 may be embodied as any type of display capable of displaying digital images or other information, such as a liquid crystal display (LCD), a light emitting diode (LED), a plasma display, a cathode ray tube (CRT), or other type of display device. In some embodiments, the display 130 may be coupled to a touch screen to allow user interaction with the surgical planning and assistance device 102.

The surgical planning and assistance device 102 further includes one or more cameras 132. Each of the cameras 132 may be embodied as a digital camera or other digital imaging device coupled to the surgical planning and assistance device 102. Each camera 132 includes an electronic image sensor, such as an active-pixel sensor (APS), e.g., a complementary metal-oxide-semiconductor (CMOS) sensor, or a charge-coupled device (CCD). In the illustrative embodiment, multiple cameras 132 are arranged in an array and are thus capable of determining distance to objects imaged by the cameras 132.

The robotic surgical device 104 may be embodied as any type of robot capable of performing the functions described herein. Illustratively, the robotic surgical device 104 is embodied as a robotic arm that may be attached to a surgical table or otherwise positioned near a patient during the orthopaedic surgical procedure. The robotic surgical device 104 includes a surgical tool 106, illustratively embodied as a surgical saw 106. In use, the robotic surgical device 104 supports the surgical saw 106 and may constrain movement of the surgical saw 106 within a resection plane specified in a surgical plan, as described further below. The surgeon may activate the surgical saw 106 and perform the resection with the surgical saw 106 while the robotic surgical device 104 constrains movement of the surgical saw 106 to the resection plane. Although illustrated with a surgical saw 106, it should be understood that, in other embodiments, the robotic surgical device 104 may include, or be used with, one or more other surgical instruments, such as, for example, surgical burrs, chisels, impactors, reamers, and other powered surgical tools. The robotic surgical device 104 may illustratively be embodied as a VELYS™ Robotic-Assisted Solution, commercially available from DePuy Synthes Products, Inc. of Warsaw, Indiana.

The surgical planning and assistance device 102 and the robotic surgical device 104 may be configured to transmit and receive data with each other and/or other devices of the system 100 over a network 114. The network 114 may be embodied as any number of various wired and/or wireless networks. For example, the network 114 may be embodied as, or otherwise include, a wired or wireless local area network (LAN), a wired or wireless wide area network (WAN), a cellular network, and/or a publicly-accessible, global network such as the Internet. As such, the network 114 include any number of additional devices, such as additional computers, routers, stations, and switches, to facilitate communications among the devices of the system 100.

As shown in FIG. 1, the system 100 further includes a number of registration tools 108. As described further below, in use, the surgical planning and assistance device 102 may track the location of the registration tools 108 in space using the array of cameras 132. For example, each registration tool 108 may include a number of hydrophobic optical reflectors arranged in a predetermined pattern visible to the cameras 132. Illustratively, the registration tools 108 include a plurality of arrays 110 configured to each be secured to one of the patient's bones, to the robotic surgical device 104, or to the surgical tool 106. Illustratively, the registration tools 108 also include a pointer 112 configured to be temporarily positioned by a surgeon relative to anatomical landmarks of the patient (e.g., with an end of the pointer 112 in contact those anatomical landmarks) while the pointer 112 is observed by the cameras 132. As such, the registration tools 108 may be used for registration and tracking of the patient's bony anatomy during the orthopaedic surgical procedure. Although illustrated as including registration tools 108 suitable for optical tracking with the cameras 132, it should be understood that in some embodiments, the system 100 may perform electromagnetic tracking or other position tracking technology for tracking the registration tools 108.

Figure 2:
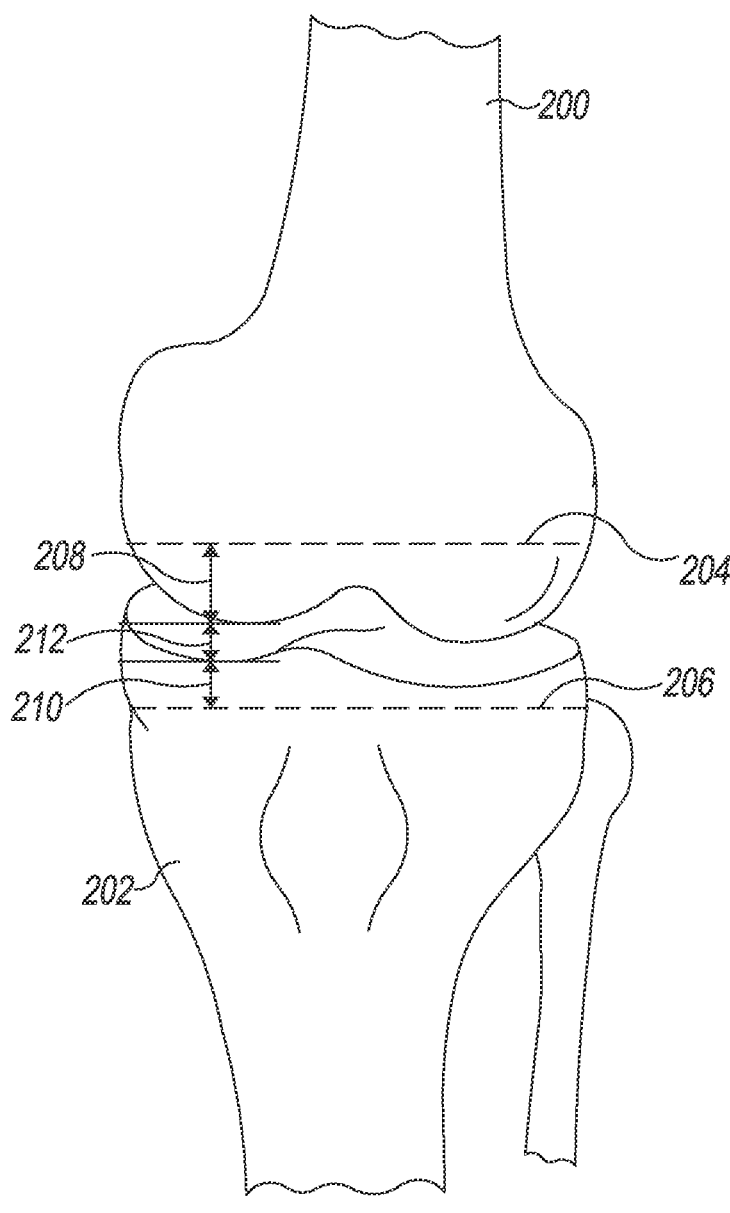
FIGS. 2 and 3 are schematic illustrations of a patient's knee joint.
Figure 3:
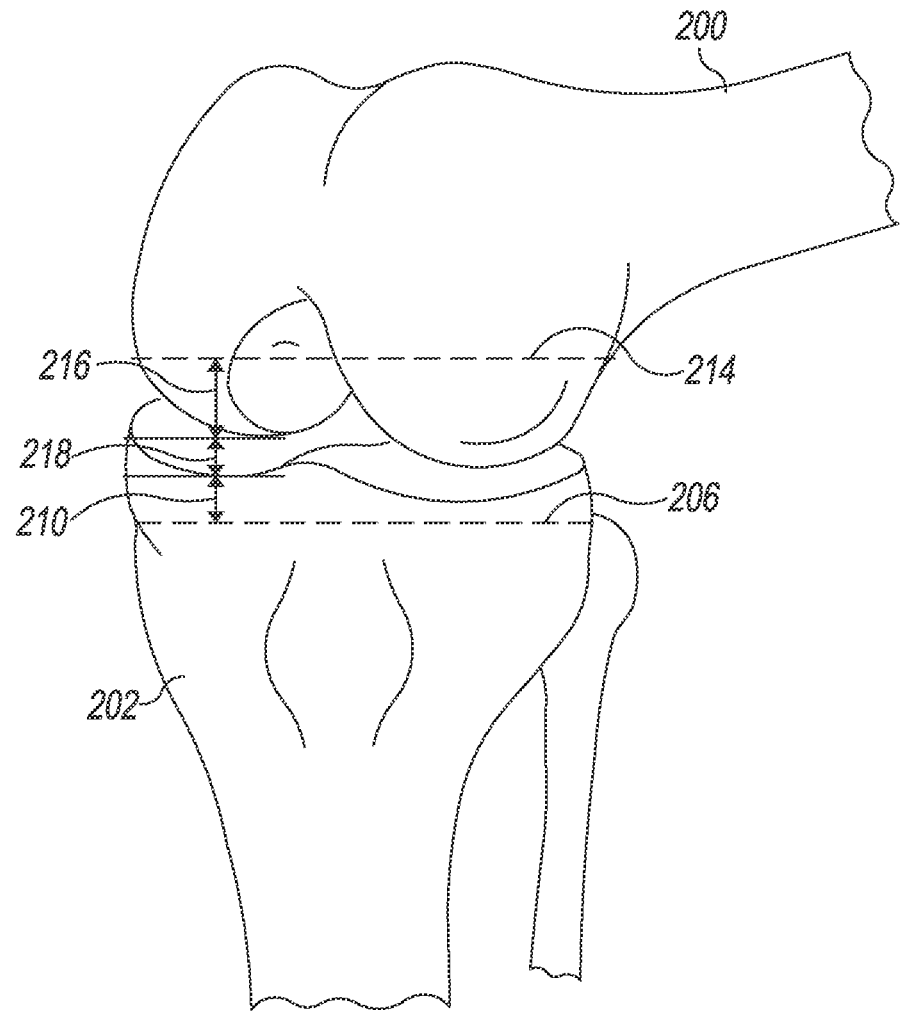

Referring now to FIGS. 2 and 3, an illustrative patient's knee joint includes a femur 200 and a tibia 202. FIG. 2 illustrates the joint in extension, and FIG. 3 illustrates the joint in flexion. As described above, during a knee arthroplasty orthopaedic surgical procedure, the surgeon makes multiple resections of the femur 200 and the tibia 202. As shown in FIG. 2, a distal femur resection 204 is made in the distal condyles of the femur 200, and a tibia resection 206 is made in the proximal end of the tibia 202. The position of the distal femur resection 204 may be defined by a distal femur resection height 208. The distal femur resection height 208 is the distance (e.g., in millimeters) from the distal-most point of a condyle of the femur 200 to the plane of the distal femur resection 204. Similarly, the position of the tibia resection 206 may be defined by a tibia resection height 210. The tibia resection height 210 is the distance (e.g., in millimeters) from the bottom point of the articular surface that is positioned opposite of the femoral condyle to the plane of the tibia resection 206. Before resections are made, the femur 200 and the tibia 202 may be separated by a bone space (or bone laxity) in extension 212. Illustratively, the bone space in extension 212 is a patient-specific value that is measured between the distal-most point of the condyle of the femur 200 and the corresponding articular surface of the tibia 202 when the knee joint is in extension.

As shown in FIG. 3, a posterior femur resection 214 is made in the posterior condyles of the femur 200. The position of the posterior femur resection 214 may be defined by a posterior femur resection height 216. The posterior femur resection height 216 is the distance (e.g., in millimeters) from the posterior-most point of the condyle of the femur 200 to the plane of posterior femur resection 214. As shown, before resections are made the femur 200 and the tibia 202 may also be separated by a bone space (or bone laxity) in flexion 218. The bone space in flexion 218 may be measured between the posterior-most point of the condyle of the femur 200 and the corresponding articular surface of the tibia 202 when the knee joint is in flexion. The bone space in extension 212 and/or the bone space in flexion 218 may be measured by the device 102 (for example, during leg-alignment registration, as described further below). Although FIGS. 2 and 3 illustrate the resection heights 208, 210, 216 and joint spaces 212, 218 on the medial side of the knee joint, it should be understood that similar resection heights, joint spaces, and other measurements may also be defined and determined for the lateral side of the knee joint. Additionally, in some embodiments the medial and lateral resection heights may differ, which may affect one or more angles of the knee joint.

Figure 4:
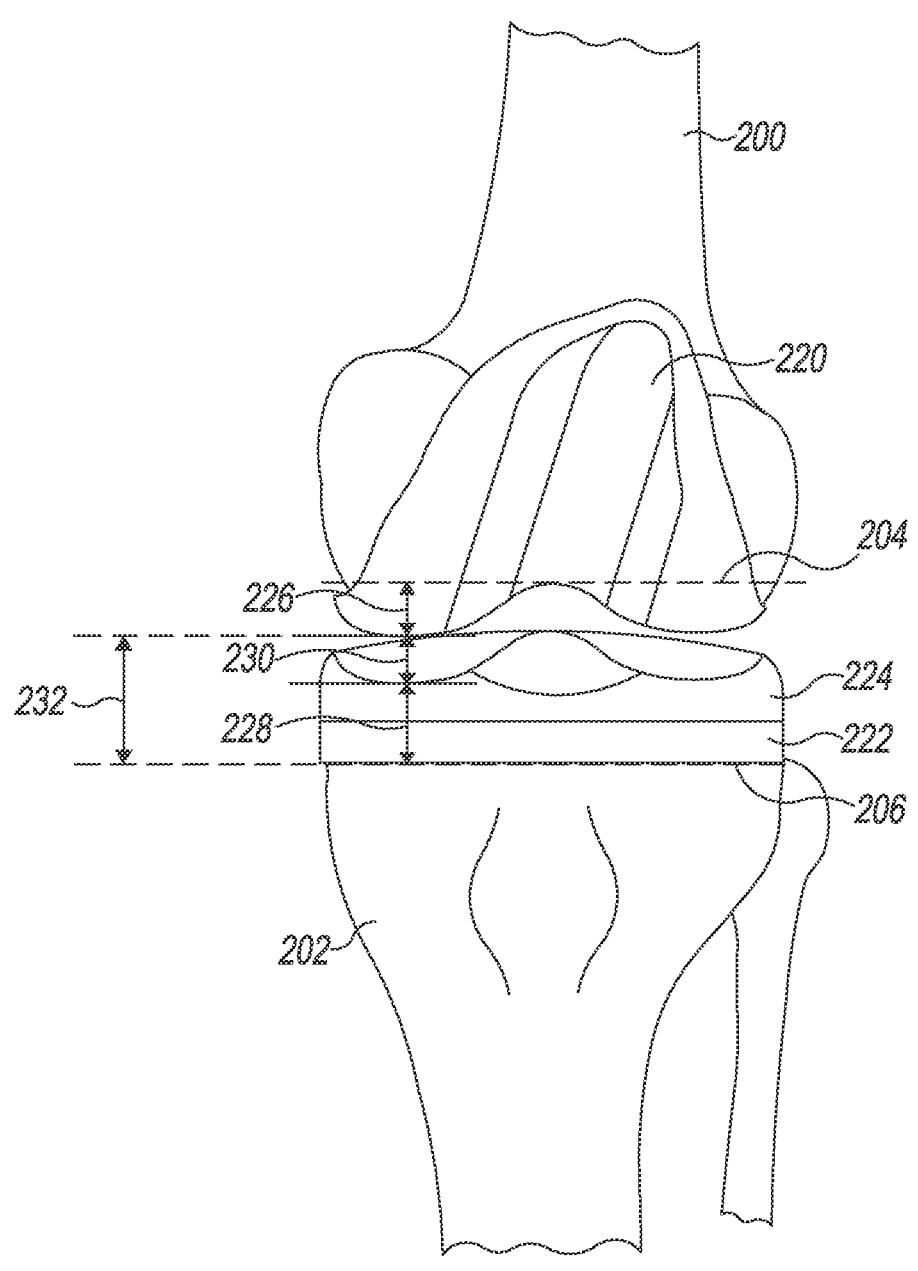
FIGS. 4 and 5 are schematic illustrations of a patient's knee joint including prosthetic components following an orthopaedic surgical procedure.
Figure 5:
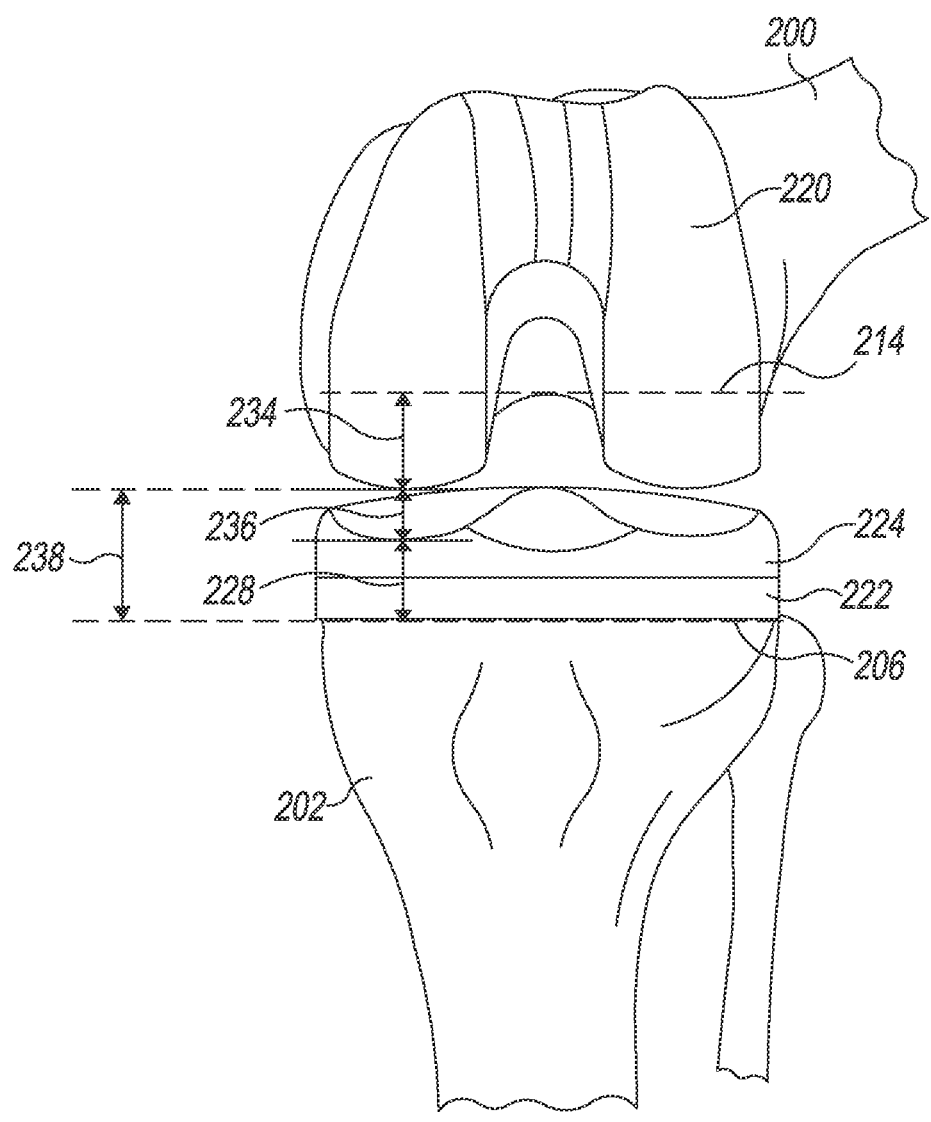

Referring now to FIGS. 4 and 5, the illustrative patient's knee joint is shown with prosthetic components located in planned positions (which may also be the final, installed positions of the prosthetic components or may be refined prior to prosthetic component installation). The prosthetic components include a femoral component 220 installed on the femur 200, a tibial tray 222 installed on the tibia 202, and an insert or bearing 224 installed on the tibial tray 222. In some embodiments (not shown), rather than including both a tibial tray 222 and a separate insert 224, the knee joint may include a unitary tibial component (e.g., an all-polymer component) that performs functions of both the tibial tray 222 and the insert 224.

As shown in FIG. 4, the femoral component 220 has a distal thickness 226, which may be measured from the distal-most point of a condyle of the femoral component 220 to the plane of the distal resection 204. As shown in FIGS. 4 and 5, the tibial tray 222 and the insert 224 have a combined thickness 228 that may be measured from the bottom point of the articular surface of the insert 224 that is positioned opposite of the femoral condyle to the plane of the tibia resection 206. As shown in FIG. 5, the femoral component 220 also has a posterior thickness 234, which may be measured from the posterior-most point of the condyle of the femoral component 220 to the plane of posterior femur resection 214. Each of the thicknesses 226, 228, 234 may vary with the type and/or size of component selected for installation. For example, an illustrative femoral component 220 may have a distal thickness 226 equal to 9 mm and a posterior thickness 234 equal to 8 mm. As another example, the combined thickness 228 may be 9 mm when used with a 5 mm insert 224. In some embodiments, the combined thickness 228 may be varied by selecting among inserts 224 with different sizes. The illustrative components 220, 222, 224 have the same thickness on both the medial and lateral side; however, in some embodiments it should be understood that one or more of the components 220, 222, 224 may have different medial and lateral thicknesses. In those embodiments, joint spaces may be determined separately for the medial and lateral sides as described below.

As shown in FIG. 4, in some situations, the distal-most point of the condyle of the femoral component 220 may be separated from the articular surface of the insert 224 by an implant space in extension 230. When the knee joint is in extension, a tibial space in extension 232 may also be defined between the femoral component 220 and the tibial resection 206. This tibial space in extension 232 includes space for the combined thickness 228 of the tibial tray 222 and the insert 224 as well as any implant space in extension 230.

Similarly, as shown in FIG. 5, in some situations, the posterior-most point of the condyle of the femoral component 220 may be separated from the articular surface of the insert 224 by an implant space in flexion 236. When the knee joint is in flexion, a tibial space in flexion 238 maybe defined between the femoral component 220 and the tibial resection 206. This tibial space in flexion 238 includes space for the combined thickness 228 of the tibial tray 222 and the insert 224 as well as any implant space in flexion 236.

The distance between the distal femur resection 204 and the tibia resection 206 may be the same for the non-implant space shown in FIG. 2 and the implant space shown in FIG. 4. This relationship may be expressed mathematically according to Equation 1, below, in which $I_e$ is the implant space in extension 230, $B_d$ is the distal femur resection height 208, $B_e$ is the bone space in extension 212, $B_t$ is the tibia resection height 210, $F_d$ is the distal femoral component thickness 226, and T is the combined thickness 228. Accordingly, the implant space in extension 230 may be expressed mathematically according to Equation 2, below.

$$F_d + T + I_e = B_d + B_e + B_t \qquad (1)$$

$$I_e = B_d + B_e + B_r - F_d - T \qquad (2)$$

Illustratively, $F_d$ and T may be determined by the size of the components in use, and $B_e$ may be a measured value. In some embodiments, $B_e$ may be measured directly. Additionally or alternatively, $B_e$ may be calculated based on the distance between the distal femur resection 204 and the tibia resection 206, which is equal to $B_d+B_e+B_t$. Thus, based on Equation 2, the implant space in extension 230 ($I_e$) may be considered a function of the distal femur resection height 208 ($B_d$) and the tibia resection height 210 ($B_t$).

Similarly, the distance between the posterior femur resection 214 and the tibia resection 206 may be the same for the non-implant space shown in FIG. 3 and the implant space shown in FIG. 5. This relationship may be expressed mathematically according to Equation 3, below, in which $I_f$ is the implant space in flexion 236, $B_p$ is the posterior femur resection height 216, $B_f$ is the bone space in flexion 218, $B_t$ is the tibia resection height 210, $F_p$ is the posterior femoral component thickness 234, and T is the combined thickness 228. Accordingly, the implant space in flexion 236 may be expressed mathematically according to Equation 4, below.

$$F_p + T + I_f = B_p + B_f + B_t \qquad (3)$$

$$I_f = B_p + B_f + B_t - F_p - T \qquad (4)$$

Illustratively, $F_p$ and T may be determined by the size of the components in use, and $B_f$ may be a measured value. In some embodiments, Br may be measured directly. Additionally or alternatively, $B_f$ may be calculated based on the distance between the posterior femur resection 214 and the tibia resection 206, which is equal to $B_p+B_f+B_t$. Thus, based on Equation 4, the implant space in flexion 236 ($I_f$) may be considered a function of the posterior femur resection height 216 ($B_p$) and the tibia resection height 210 ($B_t$). Additionally or alternatively, in some embodiments the mathematical relationships shown in Equations 1-4 may be used to determine other values, such as the tibial space in extension 232 and the tibial space in flexion 238. Further, although the joint spaces, resection heights, and component thicknesses are illustrated in FIGS. 2-5 on the medial side of the knee joint, it should be understood that similar resection heights, joint spaces, and other measurements may also be defined and determined for the lateral side of the knee joint.

Figure 6:
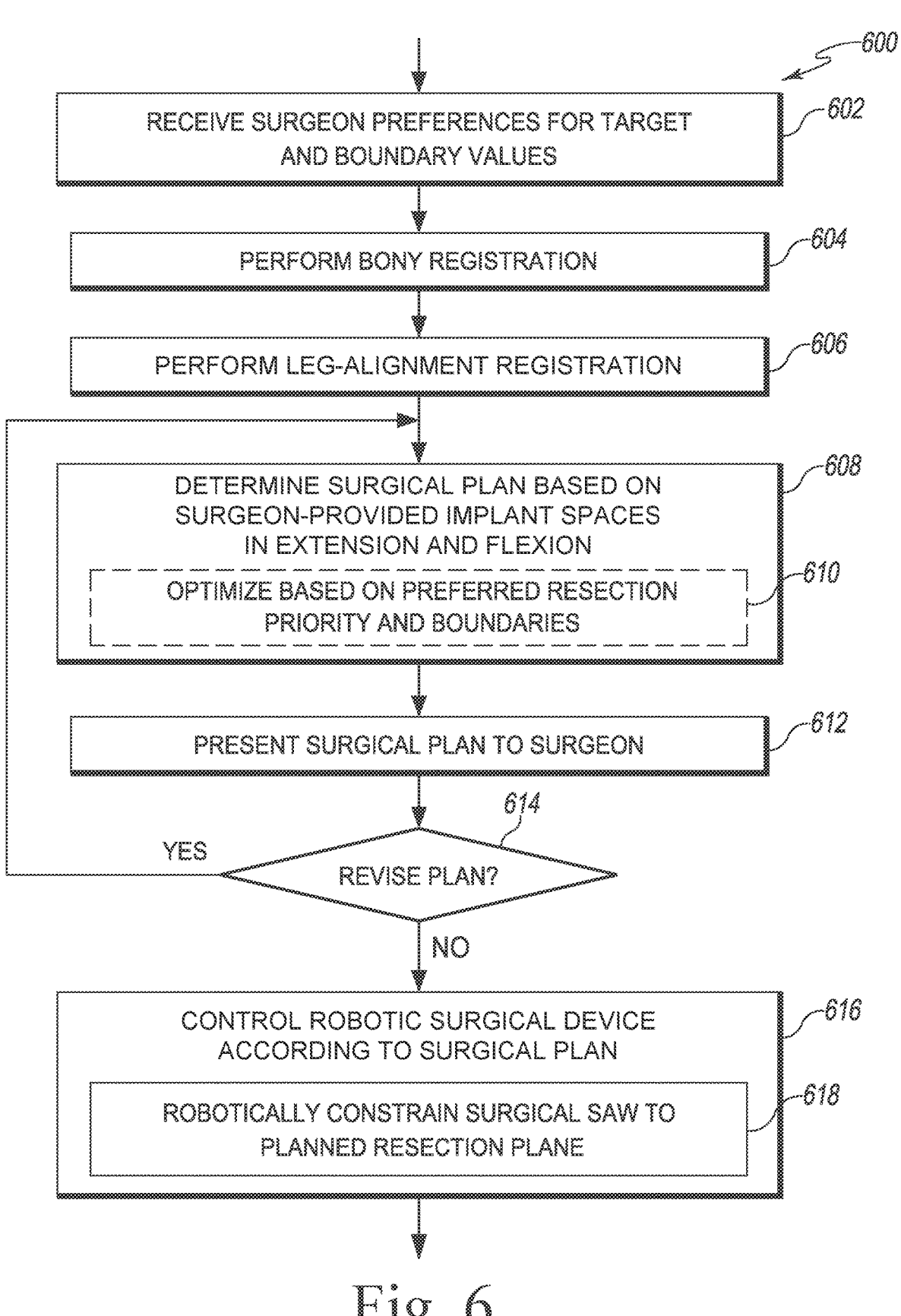
FIG. 6 is a simplified flow diagram of a method for an orthopaedic surgical procedure including automated surgical planning that may be executed by a surgical planning and assistance device of FIG. 1.

Referring now to FIG. 6, in use, the surgical planning and assistance device 102 may perform a method 600 for an orthopaedic surgical procedure with automated surgical planning. The method 600 begins with block 602, in which the device 102 receives surgeon preferences for targets and boundary values for various surgical parameters associated with the orthopaedic surgical procedure. For example, the device 102 may receive target values for the implant space in extension 230 and the implant space in flexion 236. As another example, the device 102 may receive boundary values (e.g., maximum and/or minimum values) for the distal femur resection height 208, the tibia resection height 210, and the posterior femur resection height 216. The device 102 may also receive boundary values for other surgical parameters, such as varus/valgus angle, femoral rotation, anteriorization, tibial slope, or other parameters. In some embodiments, the surgeon preferences may include relative priorities for the distal femur resection 204, the tibia resection 206, and the posterior femur resection 214. As described further below, the positions of those resections may be adjusted in order of reverse priority.

In block 604, the device 102 may perform bony registration of the patient's bony anatomy. To perform the bony registration, the surgeon may attach a bone array 110 to each of the patient's tibia and femur. The surgeon may use the pointer 112 to touch various landmarks on the patient's bony anatomy. During the registration, the device 102 uses the cameras 132 to track the position of the bone arrays 110 and the pointer 112 and thus registers the position of each landmark of the patient's bony anatomy.

As part of bony registration, the device 102 may receive a cartilage loss estimation from the surgeon or other user. The surgeon may estimate the amount of cartilage lost (in millimeters) for each of the distal medial condyle, distal lateral condyle, posterior medial condyle, posterior lateral condyle, medial tibia, and lateral tibia. The surgeon or another user may input those cartilage loss estimates to the device 102, for example using a touch screen or other input device.

During bony registration or at another time, the device 102 may prompt the surgeon or other user to verify an implant size to be used in the orthopaedic surgical procedure. The implant size may be predetermined during preoperative planning or otherwise set to an initial value. After prompting, the surgeon or other user may select a different implant size, which is stored by the device 102 for further processing.

In block 606, the device 102 performs leg-alignment registration to assess the balance of the patient's knee joint throughout a range of motion. To perform the leg-alignment registration, the surgeon may articulate the patient's knee joint through the range of motion while the device 102 uses the cameras 132 to track the position of the bone arrays 110 and thus registers the relative positions of the femur 200 and the tibia 202 at multiple points in the range of motion. The surgeon may apply stress on the knee joint as it is moved through the range of motion in order to generate gaps in the joint. In the illustrative embodiment, the device 102 may determine a bone space in extension 212 and a bone space in flexion 218 based on relative positions of the femur 200 and the tibia 202 measured during the leg-alignment registration. During some surgeries, the surgeon may perform soft-tissue release, in which case the leg-alignment registration may be repeated.

Figure 7A:
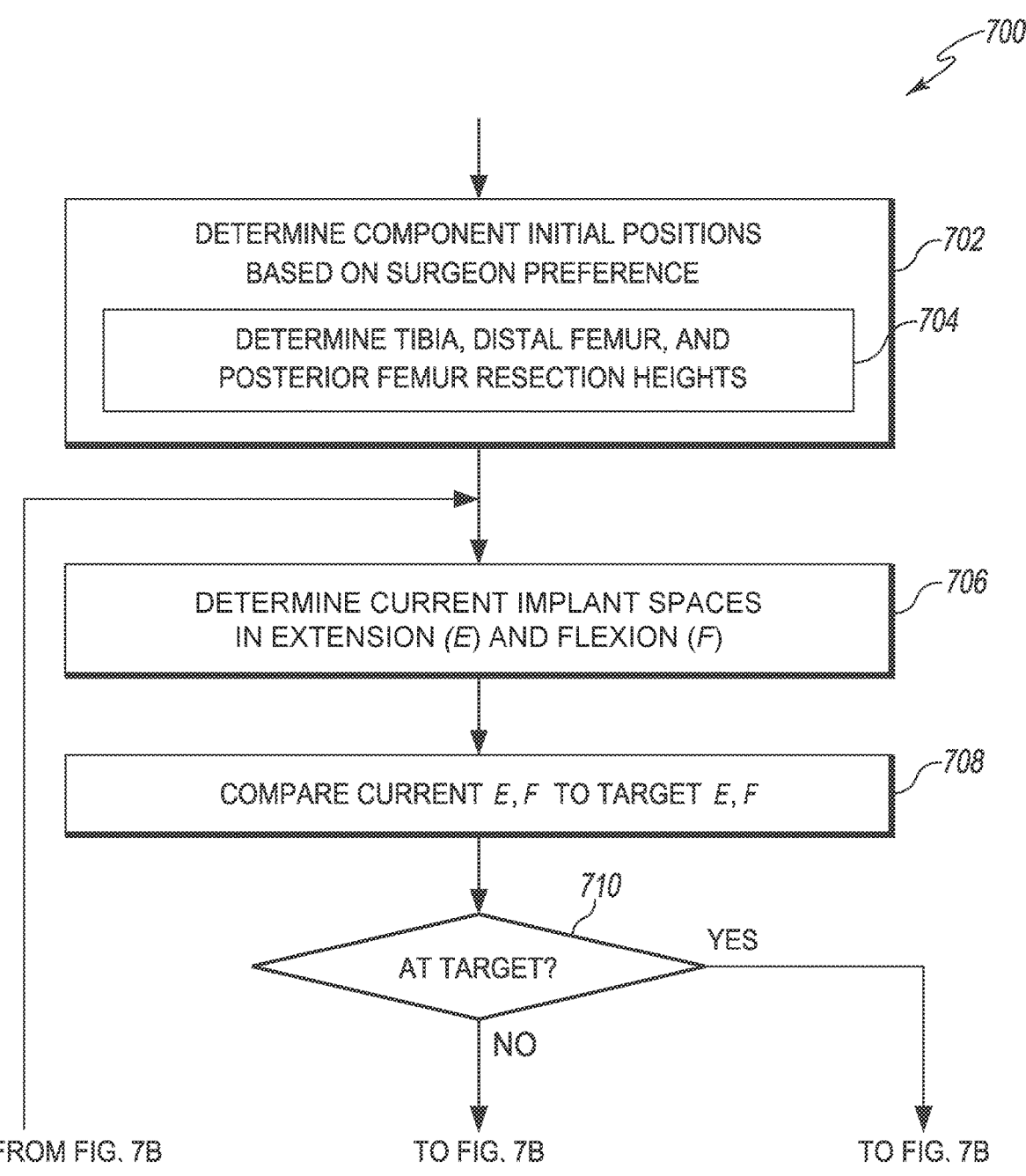
Figure 8:
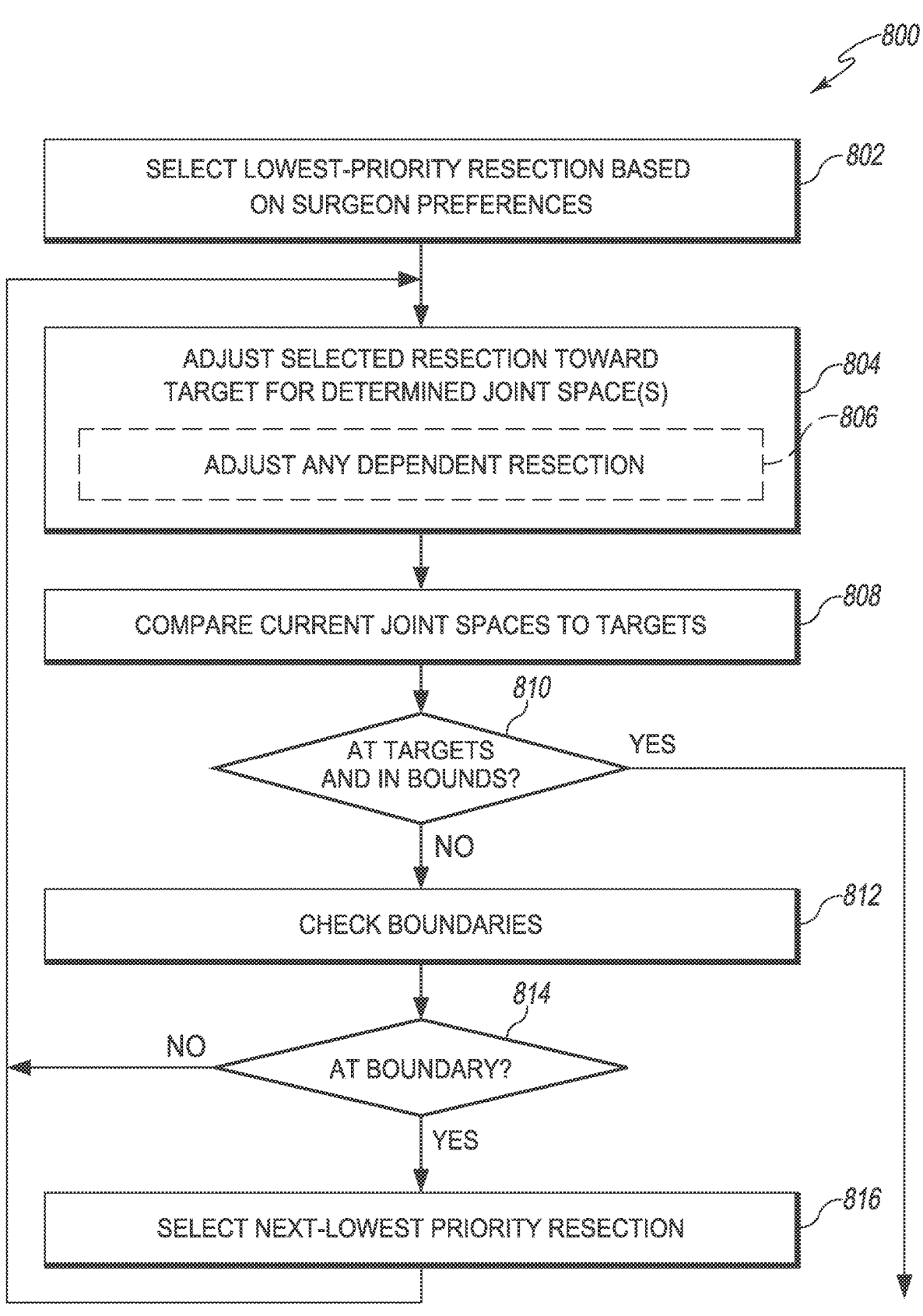
FIG. 8 is a simplified flow diagram of a method for automatically optimizing surgical plan adjustments that may be executed by the surgical planning and assistance device of FIG. 1.

In block 608, the device 102 determines a surgical plan based on target values provided by the surgeon for the implant space in extension 230 and the implant space in flexion 236. The surgical plan includes a computed, planned value for each surgical parameter associated with the orthopaedic surgical procedure. As described further below, the device 102 automatically calculates the planned values for the resection heights 208, 210, 216 that achieve the specified joint spaces 230, 236. The device 102 may calculate values for both the medial and lateral sides of the knee joint for each of those parameters. In some embodiments, the device 102 may optimize the surgical plan based on preferred resection priority and boundaries provided by the surgeon, as shown in block 610. Potential embodiments for methods for automatically determining and optimizing the surgical plan are shown in FIGS. 7A-B and 8 and described below.

Figure 9:
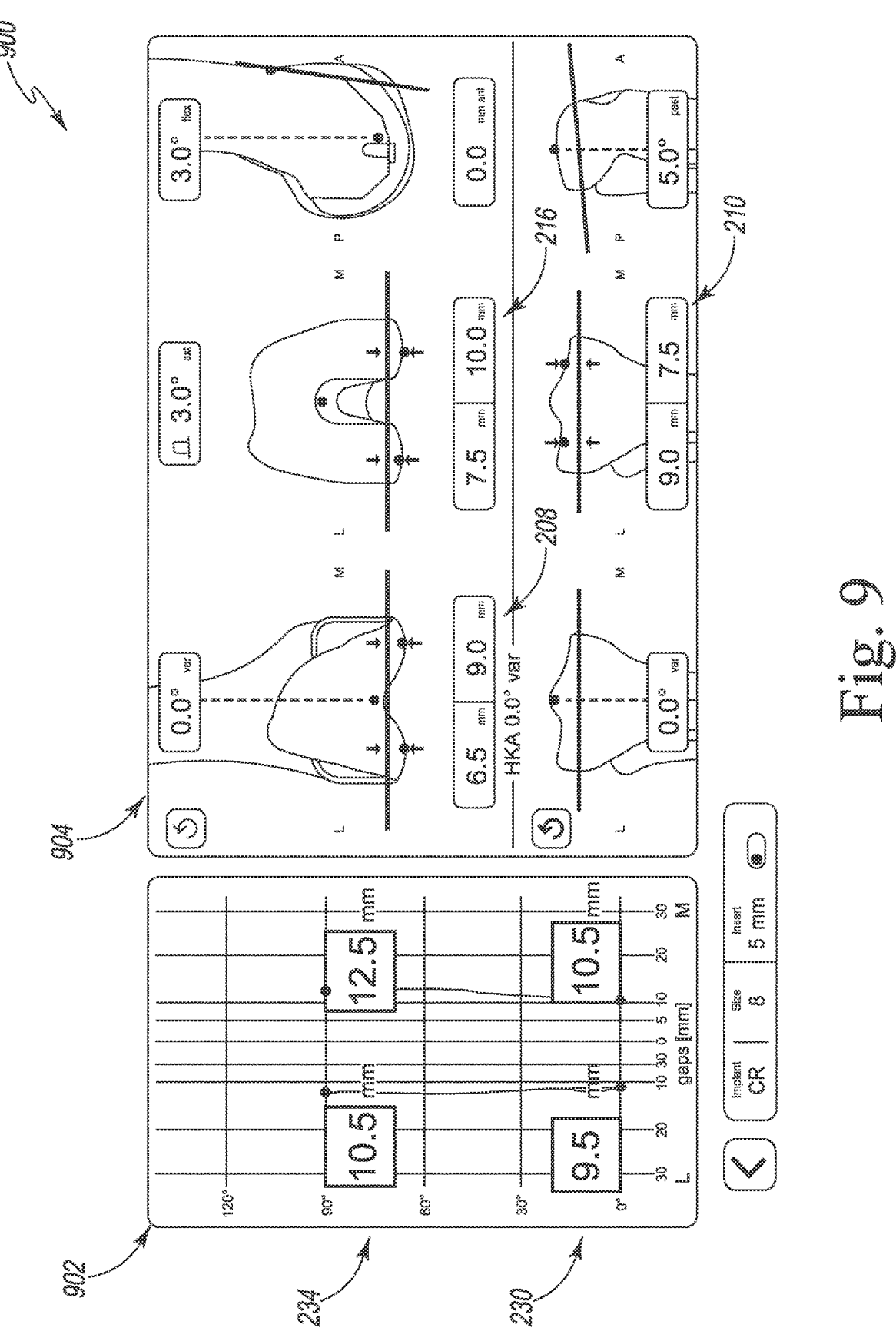
FIG. 9 is a schematic diagram illustrating one potential embodiment of a user interface that may be provided by the surgical planning and assistance device of FIG. 1 in connection with the methods of FIGS. 6-8.

After generating the surgical plan, the device 102 presents the surgical plan to the surgeon or other user in block 612. The device 102 may use any input/output device or output modality to present the surgical plan. In some embodiments, the device 102 may display numerical dimensions for resection heights, angles, position shifts, or other parameters of the surgical plan using the display 130. In some embodiments, the device 102 may graphically display the dimensions of the surgical plan 212 using the display 130. For example, the device 102 may graphically render three-dimensional models of the patient's bony anatomy along with the prosthetic components that are positioned relative to the bony anatomy according to the surgical plan. Illustrative embodiments of such a graphical interface are shown in FIG. 9 and described below.

In block 614, the device 102 receives input regarding whether the surgeon wishes to revise the surgical plan. For example, the surgeon may revise the surgical plan by modifying one or more planned values of the surgical plan. As another example, the surgeon may adjust a particular planned resection height or angle. As yet another example, the surgeon may modify the surgical plan by modifying one or more boundary values. Alternatively, the surgeon may accept the surgical plan by making no revisions. If the device 102 is instructed to revise the surgical plan, the method 600 loops back to block 608, in which the device 102 re-determines the surgical plan. If the device 102 is not instructed to revise the surgical plan, the method 600 instead advances to block 616.

In block 616, the device 102 controls the robotic surgical device 104 according to the surgical plan to assist the surgeon in performing the orthopaedic surgical procedure. The device 102 may transmit the surgical plan to the robotic surgical device 104 or otherwise cause the robotic surgical device 104 to operate according to the surgical plan. Illustratively, in block 618, the robotic surgical device 104 robotically constrains the surgical saw 106 to a planned resection plane according to the surgical plan. For example, the robotic surgical device 104 may constrain the surgical saw 106 to a resection plane defined by the distal femur resection height 208. The robotic surgical device 104 may locate this resection plane relative to the patient's anatomy by tracking the bone array 110 using the cameras 132 of the device 102, similar to the bony registration process described above. After the surgeon completes this resection, the robotic surgical device 104 may continue to robotically constrain the surgical saw 106 for additional resections based on additional parameters of the surgical plan (e.g., the tibia resection height 210 and the posterior femur resection height 216). Although illustrated and described as controlling and/or constraining the surgical saw 106, in other embodiments the robotic surgical device 104 may perform one or more different functions, such as positioning a cutting block or other surgical guide relative to the patient's anatomy. After controlling the robotic surgical device 104, the method 600 is completed. The surgeon may continue the orthopaedic surgical procedure, for example by installing one or more trial components, one or more prosthetics, or otherwise completing the orthopaedic surgical procedure.

Referring now to FIGS. 7A and 7B, in use, the surgical planning and assistance device 102 may perform a method 700 for automatically adjusting a surgical plan based on surgeon preferences. The method 700 may be executed in connection with determining the surgical plan as described above in connection with block 608 of FIG. 6. In some embodiments, the device 102 may execute the method 700 one or more times, for example to determine surgical plan parameters for both the medial and lateral side of the knee joint. The method 700 begins with block 702, in which the device 102 determines initial positions for the femoral component 220 and the tibial tray 222. In block 704, as part of determining the initial positions, the device 102 determines initial resection heights for the tibia, distal femur, and proximal femur. The initial positions, including the initial resection heights, set in blocks 702, 704 may be based upon default values and/or previously received surgeon preferences for extension and flexion spaces, resection heights, angles, tolerances, joint laxity, and/or other values that may be used to define the surgical plan. In some embodiments, the initial values for the distal femur resection height 208, the tibial resection height 210, and the posterior femur resection height 216 may be set as the thicknesses 226, 228, 234, respectively. The method 700 then proceeds to perform block 706 using the initial positions of the femoral component 220 and the tibial tray 222.

In block 706, the device 102 determines a current implant space in extension 230 and a current implant space in flexion 236. The current joint spaces 230, 236 are determined based on current values of the surgical plan as well as the bony registration and leg-alignment registration. For example, the implant space in extension 230 may be calculated using Equation 2, described above, and the current implant space in flexion 236 may be calculated using Equation 4, described above.

In block 708, the device 102 compares the current values for the implant space in extension 230 and the implant space in flexion 236 to corresponding values for the target extension space and the target flexion space. As described above, those target values may be supplied by the surgeon or other user of the device 102. In block 710, the device 102 determines whether the joint spaces 230, 236 are at their target values. If so, the method 700 is completed. As described above, the device 102 may present the surgical plan for review and/or approval by the surgeon or other user. Referring again to block 710, if the joint spaces 230, 236 do not match the corresponding target values, the method 700 advances to block 712.

In block 712, the device 102 determines one or more of the implant space in extension 230 and/or the implant space in flexion 236 to adjust, as well as a direction (e.g., positive or negative) for that adjustment. The device 102 may determine, for example, whether the current implant space in extension 230 differs from the corresponding target extension space and/or whether the current flexion space differs from the target flexion space. To determine the direction for adjustment, the device 102 may also determine whether the current implant space to be adjusted is greater than or less than the corresponding target joint space. In block 714, the device 102 may determine to adjust the implant space in extension 230. In block 716, the device 102 may determine to adjust the implant space in flexion 236. In block 718, the device 102 may determine to adjust both the implant space in extension 230 and the implant space in flexion 236.

In block 720, the device 102 adjusts one or more planned resection heights of the surgical plan toward the target for the corresponding joint space. The device 102 may increase or decrease the planned resection height(s) in order to modify the determined joint space. In some embodiments, the device 102 may also modify one or more additional, dependent planned resection heights in order to maintain the present value of the other joint space. The device 102 may adjust the planned resection heights incrementally, for example by adding or subtracting a small amount (e.g., 0.5 mm, 1 mm, or other incremental distance) from each planned resection height. Additionally or alternatively, the device 102 may adjust the planned resection heights by a different amount, such as by the difference between the current joint space value and the target joint space value.

In some embodiments, the device 102 may adjust the implant space in extension 230 by adjusting the distal femur resection height 208, as shown in block 722. For example, to increase the value of the implant space in extension 230, the device 102 may increase the distal femur resection height 208, and to decrease the value of the implant space in extension 230, the device 102 may decrease the distal femur resection height 208. Alternatively, the device 102 may adjust the implant space in extension 230 by adjusting the tibia resection height 210. When adjusting the tibia resection height 210, the device 102 may also adjust the posterior femur resection height 216 in order to preserve the current value of the implant space in flexion 236. For example, to increase the value of the implant space in extension 230, the device 102 may increase the tibia resection height 210 and decrease the posterior femur resection height 216 by the same amount. As another example, to decrease the value of the implant space in extension 230, the device 102 may decrease the tibia resection height 210 and increase the posterior femur resection height 216 by the same amount.

In some embodiments, the device 102 may adjust the implant space in flexion 236 by adjusting the posterior femur resection height 216, as shown in block 724. For example, to increase the value of the implant space in flexion 236, the device 102 may increase the posterior femur resection height 216, and to decrease the value of the implant space in flexion 236, the device 102 may decrease the posterior femur resection height 216. Alternatively, the device 102 may adjust the implant space in flexion 236 by adjusting the tibia resection height 210. When adjusting the tibia resection height 210, the device 102 also adjusts the distal femur resection height 208 in order to preserve the current value of the implant space in extension 230. For example, to increase the value of the implant space in flexion 236, the device 102 may increase the tibia resection height 210 and decrease the distal femur resection height 208 by the same amount. As another example, to decrease the value of the implant space in flexion 236, the device 102 may decrease the tibia resection height 210 and increase the distal femur resection height 208 by the same amount.

In some embodiments, the device 102 may adjust both the implant space in extension 230 and the implant space in flexion 236 by adjusting the tibia resection height 210, as shown in block 726. For example, to increase the value of the joint spaces 230, 236, the device 102 may increase the tibia resection height 210, and to decrease the value of the joint spaces 230, 236 the device 102 may decrease the tibia resection height 210. Alternatively, the device 102 may adjust both the implant space in extension 230 and the implant space in flexion 236 by adjusting the distal femur resection height 208 and the posterior femur resection height 216. For example, to increase the value of the joint spaces 230, 236, the device 102 may increase the distal femur resection height 208 and the posterior femur resection height 216, and to decrease the value of the joint spaces 230, 236 the device 102 may decrease the distal femur resection height 208 and the posterior femur resection height 216. When the joint spaces 230, 236 differ from their corresponding target values in different directions (e.g., one joint space is larger than the target and the other joint space is smaller than the target), the device 102 may independently adjust each of the joint spaces 230, 236 as described above.

After adjusting the planned resection heights in the surgical plan, the method 700 loops back to block 706, in which the device 102 recalculates the current implant space in extension 230 and the current implant space in flexion 236 and may continue adjusting the surgical plan as described above.

Referring now to FIG. 8, in use, the surgical planning and assistance device 102 may perform a method 800 for automatically optimizing surgical plan adjustments. The method 800 may be executed, for example, in connection with adjusting one or more planned resection heights as described above in connection with block 720 of FIG. 7B. The method 800 begins with block 802, in which the device 102 selects a lowest-priority resection of the distal femur resection 204, the tibia resection 206, and the posterior femur resection 214 based on surgeon preference. The surgeon preferences may be received from the surgeon or other user or otherwise predetermined. For example, the surgeon or other user may configure a predetermined ranked list of the distal femur resection 204, the tibia resection 206, and the posterior femur resection 214. As described further below, the lowest-ranked resection(s) are the first to be modified when adjusting the surgical plan.

In block 804, the device 102 adjusts the resection height for the selected resection toward the corresponding target for one or more of the joint spaces 230, 236. For example, as described above, the device 102 may determine to adjust the implant space in extension 230 and/or the implant space in flexion 236. The device 102 may incrementally or otherwise adjust the selected resection height(s) as described above. In some embodiments, in block 806 the device 102 may adjust a dependent resection height. For example, if the device 102 adjusts the tibia resection height 210 when adjusting the implant space in extension 230, the device 102 may also adjust the posterior femur resection height 216 by a corresponding amount to preserve the current value of the implant space in flexion 236. As another example, if the device 102 adjusts the tibia resection height 210 when adjusting the implant space in flexion 236, the device 102 may also adjust the distal femur resection height 208 by a corresponding amount to preserve the current value of the implant space in extension 230.

In block 808, the device 102 compares the current values for the implant space in extension 230 and the implant space in flexion 236 to corresponding values for the target extension space and the target flexion space. As described above, those target values may be supplied by the surgeon or other user of the device 102. In block 810, the device 102 determines whether the joint spaces 230, 236 are at their target values and within boundaries set for the joint spaces 230, 236. If so, the method 800 is completed. As described above, the device 102 may present the surgical plan for review and/or approval by the surgeon or other user. Referring again to block 810, if the joint spaces 230, 236 do not match the corresponding target values or are outside of boundaries, the method 800 advances to block 812.

In block 812, the device 102 checks the current surgical plan against one or more boundaries. The boundaries may be provided by the surgeon or other user, for example as one or more surgeon preferences. The boundaries may include minimum and maximum resection heights for one or more of the resections 204, 206, 214. Thus, the device 102 may compare the current distal femur resection height 208, tibia resection height 210, and/or posterior femur resection height 216 to the predetermined boundaries. As another example, the boundaries may include maximum and/or minimum values for one or more other surgical parameters, such as femoral distal varus/valgus angle, tibial varus/valgus angle, hip-knee-ankle (HKA) alignment angle, femoral rotation angle, tibial slope, femoral component anteriorization/posteriorization, and/or other surgical parameters. Values for those parameters may be determined based on one or more of the resection heights 208, 210, 216. For example, the femoral distal varus/valgus angle may be determined based on the distal femur resection heights 208 for the medial and lateral condyles combined with the distance between the condyles, the tibial varus/valgus angle may be determined based on the medial and lateral tibia resection heights 210, the HKA alignment angle may be determined based on the femoral distal varus/valgus angle and the tibial varus/valgus angle, the femoral rotation angle may be determined based on the medial and lateral posterior femur resection heights 216 and the distance between the condyles, and the femoral component anteriorization/posteriorization may be determined based on the medial and lateral posterior femur resection heights 216.

In block 814, the device 102 checks whether the surgical plan has met a boundary. If not, the method 800 loops back to block 804, in which the device 102 may continue to adjust the currently selected resection height. If the surgical plan has met a boundary, the method 800 advances to block 816, in which the device 102 selects the next-lowest priority of the distal femur resection 204, the tibia resection 206, and the posterior femur resection 214 based on the surgeon preference. After selecting the next-lowest resection, the method 800 loops back to block 804 to adjust the corresponding selected resection height. Thus, the method 800 may continue adjusting resection heights until the target joint space value is achieved.

As an illustrative example, a surgeon may specify that the distal femur resection height 208 has lowest priority, followed by the tibia resection height 210 and the posterior femur resection height 216 in increasing priority order. In order to adjust the implant space in extension 230, the device 102 may adjust the distal femur resection height 208 until a minimum or maximum boundary is met. The device 102 may then adjust the tibia resection height 210 any remaining amount required for the implant space in extension 230 to reach the corresponding target extension space. Note that as the device 102 adjusts the tibia resection height 210, the device may also adjust the posterior femur resection height 216 by a corresponding amount to preserve the present value of the implant space in flexion 236.

Referring now to FIG. 9, an illustrative embodiment of a user interface 900 that may be provided by the device 102 is shown. In particular, the interface 900 may be a graphical user interface for viewing and/or editing the surgical plan that may be displayed on the display 130 of the device 102. The interface 900 includes user interface controls 902 that allow a surgeon or other user to specify target joint space values. Illustratively, the controls 902 include inputs for both medial and lateral target values for the implant space in extension 230 and the implant space in flexion 236. The controls 902 may also include a graph displaying current values for the joint spaces 230, 236. After receiving target values for the implant space in extension 230 and the implant space in flexion 236, the device 102 may determine a surgical plan including resection heights as described above.

The interface 900 further includes user interface elements 904 that display planned parameters of the surgical plan. Illustratively, the elements 904 include graphical illustrations and text labels displaying current planned values for the distal femur resection height 208, the tibia resection height 210, and the posterior femur resection height 216. The user interface elements 904 may also display other planned parameters of the surgical plan, such as varus/ valgus angle, femoral rotation, anteriorization, tibial slope, or other parameters. In some embodiments, those parameters may be calculated based on or otherwise depend on the distal femur resection height 208, the tibia resection height 210, and/or the posterior femur resection height 216. As shown in FIG. 9, those user interface elements 904 may be determined based on the target values input using the controls 902, and thus may be embodied as text labels or other read-only user interface elements.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method for automatically generating a surgical plan for an orthopaedic surgical procedure, the method comprising:

receiving, by a computer system, a set of target joint space values, wherein the set of target joint space values comprises a target extension space value and a target flexion space value, initializing, by the computer system, a surgical plan for the orthopaedic surgical procedure, wherein the surgical plan comprises planned resection heights including at least a distal femur resection height, a posterior femur resection height, and a tibia resection height, determining, by the computer system, a set of current joint space values based on the surgical plan, and adjusting, by the computer system, one or more planned resection heights of the surgical plan until the set of current joint space values matches the set of target joint space values, wherein adjusting the one or more planned resection heights comprises:

selecting a first planned resection height having a lowest priority setting from among the distal femur resection height, the posterior femur resection height, and the tibia resection height, adjusting the first planned resection height until a first boundary setting is met, in response to the boundary setting being met, selecting a second planned resection height having a next-lowest priority setting from among the distal femur resection height, the posterior femur resection height, and the tibia resection height, and adjusting the second planned resection height until a second boundary setting is met.

2. The method of claim 1, further comprising:

performing, by the computer system, bony registration of bony anatomy of a patient, and performing, by the computer system, leg-alignment registration on the patient, wherein determining the set of current joint space values comprises determining the set of current joint space values based on the surgical plan, the bony registration, and the leg-alignment registration.

3. The method of claim 2, wherein determining the set of current joint space values comprises determining (i) a current implant space in extension value as a function of the distal femur resection height and the tibia resection height, and (ii) a current implant space in flexion value as a function of the posterior femur resection height and the tibia resection height.

4. The method of claim 3, wherein the current implant space in extension value comprises the distal femur resection height, added to a bone space in extension value measured during the leg-alignment registration, added to the tibia resection height, less a distal femoral component thickness, and less a tibial component thickness.

5. The method of claim 3, wherein the current implant space in flexion value comprises the posterior femur resection height, added to a bone space in flexion value measured during the leg-alignment registration, added to the tibia resection height, less a posterior femoral component thickness, and less a tibial component thickness.

6. The method of claim 5, wherein the current implant space in extension value comprises the distal femur resection height, added to a bone space in extension value measured during the leg-alignment registration, added to the tibia resection height, less a distal femoral component thickness, and less the tibial component thickness.

7. The method of claim 1, wherein adjusting the one or more planned resection heights of the surgical plan comprises:

selecting a joint space for adjustment based on the current joint space value for the joint space not matching the target joint space value for the joint space, and selecting the one or more planned resection heights to adjust based on the joint space selected for adjustment.

8. The method of claim 7, wherein the joint space selected for adjustment comprises an extension space, and wherein adjusting the one or more planned resection heights comprises one of (i) adjusting the distal femur resection height toward the target extension space value or (ii) adjusting the tibia resection height toward the target extension space value and adjusting the posterior femur resection height to preserve a current flexion space value.

9. The method of claim 7, wherein the joint space selected for adjustment comprises a flexion space, and wherein adjusting the one or more planned resection heights comprises one of (i) adjusting the posterior femur resection height toward the target flexion space value or (ii) adjusting the tibia resection height toward the target flexion space value and adjusting the distal femur resection height to preserve a current extension space value.

10. The method of claim 7, wherein the joint space selected for adjustment comprises an extension space and a flexion space, and wherein adjusting the one or more planned resection heights comprises one of (i) adjusting the tibia resection height toward the target extension space value and the target flexion space value or (ii) adjusting the distal femur resection height toward the target extension space value and adjusting the posterior femur resection height toward the target flexion space value.

11. The method of claim 1, wherein the boundary settings and the priority settings reflect preferences of a surgeon performing the orthopaedic surgical procedure.

12. The method of claim 1, wherein the first boundary setting comprises a minimum or a maximum resection height associated with the first planned resection height.

13. The method of claim 1, wherein the first boundary setting comprises a minimum or maximum varus/valgus angle or a minimum or maximum hip-knee-ankle (HKA) angle, wherein the surgical plan comprises planned medial resection heights and planned lateral resection heights, and wherein the set of target joint space values comprises medial target joint space values and lateral target joint space values.

14. The method of claim 1, further comprising controlling, by the computer system, a robotic surgical device to achieve the planned resection heights of the surgical plan.

15. The method of claim 14, wherein controlling the robotic surgical device comprises robotically constraining a surgical saw in a geometric plane defined by one of the planned resection heights of the surgical plan.

16. A method for automatically generating a surgical plan for an orthopaedic surgical procedure, the method comprising:

initializing, by a computer system, a surgical plan for the orthopaedic surgical procedure, wherein the surgical plan comprises a distal femur resection height, a posterior femur resection height, and a tibia resection height, selecting, by the computer system, a first planned resection height having a first priority setting from among the distal femur resection height, the posterior femur resection height, and the tibia resection height of the surgical plan, adjusting, by the computer system, the first planned resection height until either (i) each current joint space value affected by the first planned resection height matches a corresponding target joint space value or (ii) a first boundary setting is met, after adjusting the first planned resection height, selecting, by the computer system, a second planned resection height having a second priority setting from among the distal femur resection height, the posterior femur resection height, and the tibia resection height of the surgical plan, and adjusting, by the computer system, the second planned resection height until either (i) each current joint space value affected by the second planned resection height matches a corresponding target joint space value or (ii) a second boundary setting is met.

17. The method of claim 16, further comprising:

after adjusting the second planned resection height, selecting, by the computer system, a third planned resection height having a third priority setting from among the distal femur resection height, the posterior femur resection height, and the tibia resection height of the surgical plan, adjusting, by the computer system, the third planned resection height until either (i) each current joint space value affected by the third planned resection height matches a corresponding target joint space value or (ii) a third boundary setting is met.

18. The method of claim 16, wherein the first and second priority settings and the first and second boundary settings reflect preferences of a surgeon performing the orthopaedic surgical procedure.

19. The method of claim 16, wherein the first boundary setting comprises a minimum or a maximum resection height associated with the first planned resection height, and wherein the second boundary setting comprises a minimum or a maximum resection height associated with the second planned resection height.

20. The method of claim 16, wherein the distal femur resection height of the surgical plan comprises a medial distal femur resection height and a lateral distal femur resection height, wherein the posterior femur resection height of the surgical plan comprises a medial posterior femur resection height and a lateral posterior femur resection height, and wherein at least one of the first and second boundary settings comprises a minimum or maximum varus/valgus angle or a minimum or maximum hip-knee-ankle (HKA) angle.

* * * * *